(12) United States Patent
Britto et al.

(10) Patent No.: US 6,840,918 B1
(45) Date of Patent: Jan. 11, 2005

(54) PUMPING BREAST MILK

(75) Inventors: James J. Britto, Westport, MA (US); Shiu Hung Li, Taipo (HK)

(73) Assignee: The First Years Inc., Avon, MA (US)

( * ) Notice: Subject to any disclaimer, the term of this patent is extended or adjusted under 35 U.S.C. 154(b) by 361 days.

(21) Appl. No.: 09/908,053

(22) Filed: Jul. 18, 2001

Related U.S. Application Data

(63) Continuation of application No. 09/687,452, filed on Oct. 13, 2000, now Pat. No. 6,673,036.
(60) Provisional application No. 60/159,344, filed on Oct. 13, 1999.

(51) Int. Cl.[7] ................................................ A61M 1/06
(52) U.S. Cl. ......................................... 604/74; 604/364
(58) Field of Search ............................ 604/73–76, 346, 604/48, 315, 316; 417/435, 440

(56) References Cited

U.S. PATENT DOCUMENTS

| | | |
|---|---|---|
| 823,316 A | 6/1906 | Andersen |
| 1,184,293 A | 5/1916 | Zeratsky |
| 1,259,309 A | 3/1918 | Somers |
| 1,596,520 A | 8/1926 | Eskholme et al. |
| 3,238,937 A | 3/1966 | Stein |
| 3,382,867 A | 5/1968 | Reaves |
| 3,931,795 A | 1/1976 | Duncan |
| 3,990,816 A | 11/1976 | Köhler et al. |
| 4,263,912 A | 4/1981 | Adams |
| 4,486,157 A | 12/1984 | Hayashi |
| 4,607,596 A | 8/1986 | Whittlestone et al. |
| 4,673,388 A | 6/1987 | Schlensog et al. |
| 4,772,262 A | 9/1988 | Grant et al. |
| 4,813,932 A | 3/1989 | Hobbs |
| 4,857,051 A | 8/1989 | Larsson |
| 4,929,229 A | 5/1990 | Larsson |
| 4,941,433 A | 7/1990 | Hanauer |

(List continued on next page.)

FOREIGN PATENT DOCUMENTS

| | | |
|---|---|---|
| CA | 2115824 | 8/1994 |
| DE | 540 934 | 12/1931 |
| DE | 24 51 953 | 5/1974 |
| DE | 28 07 646 | 8/1978 |
| DE | 32 28 725 A1 | 2/1984 |
| EP | 0 123 269 A2 | 10/1984 |
| EP | 0 604 070 B1 | 6/1994 |
| EP | 0 611 578 B1 | 8/1994 |
| EP | 0 733 376 A2 | 9/1996 |
| FR | 599054 | 1/1926 |
| GB | 271857 | 10/1927 |
| GB | 762701 | 12/1956 |
| GB | 2 082 920 A | 3/1982 |
| GB | 2 127 293 A | 4/1984 |
| NZ | 168234 | 9/1921 |
| SE | 158 976 | 5/1957 |
| WO | WO 90/11097 | 10/1990 |
| WO | WO 97/05913 | 2/1997 |
| WO | WO 99/44650 | 9/1999 |
| WO | WO 99/51882 | 10/1999 |
| WO | WO 00/41744 | 7/2000 |
| WO | WO 00/41745 | 7/2000 |
| WO | WO 00/57934 | 10/2000 |

*Primary Examiner*—David A. Scherbel
*Assistant Examiner*—Huyen Le
(74) *Attorney, Agent, or Firm*—Fish & Richardson P.C.

(57) ABSTRACT

A portable, electric breast pump has an electronic controller adapted to track time and operate a solenoid to automatically maintain a predetermined suction and release rhythm as a function of time to mimic the natural sucking rhythm of an infant. Suction is produced by a continuously running diaphragm pump. A needle valve permits user vacuum level adjustment, but no other user control is required. A flapper valve in the top of the bottle reduces the suction rise time but incorporates a fixed amount of leakage to build a small amount of bottle pressure for pulling collected milk into the bottle during the release portion of the cycle. An improved bulkhead design helps to keep milk from entering the diaphragm pump if the unit is shaken or turned on its side.

27 Claims, 7 Drawing Sheets

U.S. PATENT DOCUMENTS

| | | | |
|---|---|---|---|
| 4,961,726 | A | 10/1990 | Richter |
| 4,964,851 | A | 10/1990 | Larsson |
| 5,007,899 | A | 4/1991 | Larsson |
| 5,076,769 | A | 12/1991 | Shao |
| 5,304,129 | A | 4/1994 | Forgach |
| 5,514,166 | A | 5/1996 | Silver et al. |
| 5,542,921 | A | 8/1996 | Meyers et al. |
| 5,571,084 | A | 11/1996 | Palmer |
| 5,586,518 | A | 12/1996 | Carrano |
| 5,590,648 | A | 1/1997 | Mitchell et al. |
| 5,601,531 | A | 2/1997 | Silver |
| 5,616,125 | A | 4/1997 | Jelks |
| 5,676,525 | A | 10/1997 | Berner et al. |
| 5,720,722 | A | 2/1998 | Lockridge |
| 5,749,850 | A | 5/1998 | Williams et al. |
| 5,776,098 | A | 7/1998 | Silver et al. |
| 5,810,772 | A | 9/1998 | Niederberger |
| 5,902,267 | A | 5/1999 | Medo |
| 5,954,690 | A | 9/1999 | Larsson |
| 6,045,529 | A * | 4/2000 | Nuesch ........................ 604/74 |
| 6,090,065 | A | 7/2000 | Giles |
| 6,110,140 | A | 8/2000 | Silver |
| 6,139,521 | A | 10/2000 | Larsson |
| 6,257,847 | B1 | 7/2001 | Silver et al. |
| 6,383,163 | B1 * | 5/2002 | Kelly et al. ................... 607/74 |

\* cited by examiner-

PUMPING BREAST MILK

This is a continuation of U.S. application Ser. No. 09/687,452, filed Oct. 13, 2000 now U.S. Pat. No. 6,673,036 and claiming priority from provisional application No. 60/159,344, filed Oct. 13, 1999.

BACKGROUND

This invention relates generally to devices and methods for drawing milk from a human breast.

Many mothers rely on pumps to extract their breast milk. The more such pumps are automated and simulate the natural sucking rhythms of an infant, the easier it can be for a mother to relax and allow her milk to "let down" and flow. Pumps in common use include manually operated mechanical pumps. Which require the user to repeatedly manipulate a lever or pedal to produce suction. and electrical pumps, which run on either DC battery or AC line voltage.

With portable pumps, especially ones with electric vacuum sources, it is preferred that the milk only enters the easily washed storage bottle connected to the breast hood. Particularly, milk should be kept from inaccessible vacuum passages and pumping hardware which is not easily cleaned. Many electric pumps, for instance, come with instructions that caution against allowing the pump to tip over or lie on its side with milk in the bottle, as the milk may flow through the vacuum port and into the pumping chamber.

SUMMARY

According to one aspect of the invention, a receptacle bulkhead for a portable pumping device for drawing milk from a human breast is provided. The pumping device has a milk receptacle and a vacuum source for applying suction to a hood configured to receive the breast, and the receptacle bulkhead is configured to separately connect the vacuum source and the hood to the milk receptacle. The bulkhead has a housing defining an internal chamber, a milk inlet conduit, a milk outlet conduit and a vacuum port. The milk inlet conduit provides communication between the hood and the internal chamber and extends from one side of the internal chamber with the portable pumping device in an upright position for normal use, such that entering milk tends to flow along a lower side of the conduit. The milk outlet provides communication between the internal chamber and the milk receptacle, and is disposed at a lower end of the internal chamber with the portable pumping device in its upright position. The vacuum port provides communication between the vacuum source and the internal chamber through a vacuum inlet passage within the receptacle bulkhead. The vacuum inlet passage extends a distance along the milk inlet conduit and is separated from the lower side of the conduit, such that with the pumping device in its upright position milk entering from the hood will tend to avoid the vacuum inlet passage and, with the pumping device in a sideways position with the milk inlet conduit extending upward, milk from the receptacle will be inhibited from entering the vacuum inlet passage.

In a presently preferred construction, the internal chamber has a domed upper surface and the vacuum port is disposed at an upper apex of the domed upper surface.

The housing may be of a unitary molded piece of transparent plastic, for example, and may form a top for the milk receptacle, with the milk outlet making a threaded connection between the milk receptacle and the bulkhead housing.

Preferably, the vacuum inlet passage extends beyond the milk outlet toward the hood.

According to another aspect of the invention, a breast pump for drawing milk from a human breast includes a hood configured to receive the breast, a milk receptacle in communication with the hood for storing milk from the breast, a vacuum source for applying suction to the hood, and a one-way valve disposed between the hood and the milk receptacle. The valve includes a cup-shaped valve body with a hole through its bottom, and a flexible membrane flap. The flap is arranged to cover the hole through the valve body when suction is applied to the hood, inhibiting flow between the hood and the milk receptacle, such that milk from the hood is collected in the cup on top of the membrane flap, and to flex, under weight of the collected milk, to expose the hole when hood suction is released, allowing the collected milk to flow from the valve body into the milk receptacle.

In one preferred embodiment, the valve cup is retained in a bulkhead constructed to provide communication between the hood, the milk receptacle, and the vacuum source, with the valve cup engaging the bulkhead at an interface constructed to provide a predetermined amount of air leakage around the valve, between the bulkhead and the milk receptacle, when suction is applied to the hood.

According to another aspect of the invention, a breast pump for drawing milk from a human breast includes a hood configured to receive the breast, a milk receptacle in communication with the hood for storing milk from the breast, a vacuum source for applying suction to the hood, a bulkhead constructed to provide communication between the hood, the milk receptacle, and the vacuum source, and a one-way valve disposed between the hood and the milk receptacle and engaging the bulkhead at an interface. The valve is constructed to close when suction is applied to the hood, and to open when suction is released to let collected milk flow into the milk receptacle. The interface between the valve and the bulkhead is constructed to provide a predetermined amount of air leakage around the valve, between the bulkhead and the milk receptacle, when suction is applied to the hood, for transferring vacuum to the milk receptacle during suction for pulling collected milk into the milk receptacle when suction is released.

Other aspects of the invention include methods of using the above-described pumping devices to extract milk from a human breast. For example, the method of using the pumping device of the first aspect of the invention includes holding the hood of the pumping device against the breast, and activating the pumping device to begin applying repeating pressure cycles to the breast to extract milk. The controller of the pumping device regulates the frequency and intervals of the pressure cycles to be effectively independent of suction, flow rates and power levels.

The improved bulkhead design of the invention can help to avoid milk entering the main body of the pump and pumping chamber, facilitating cleaning. Other features and advantages will be apparent from the following embodiment description.

DETAILED DESCRIPTION

Figure 1:
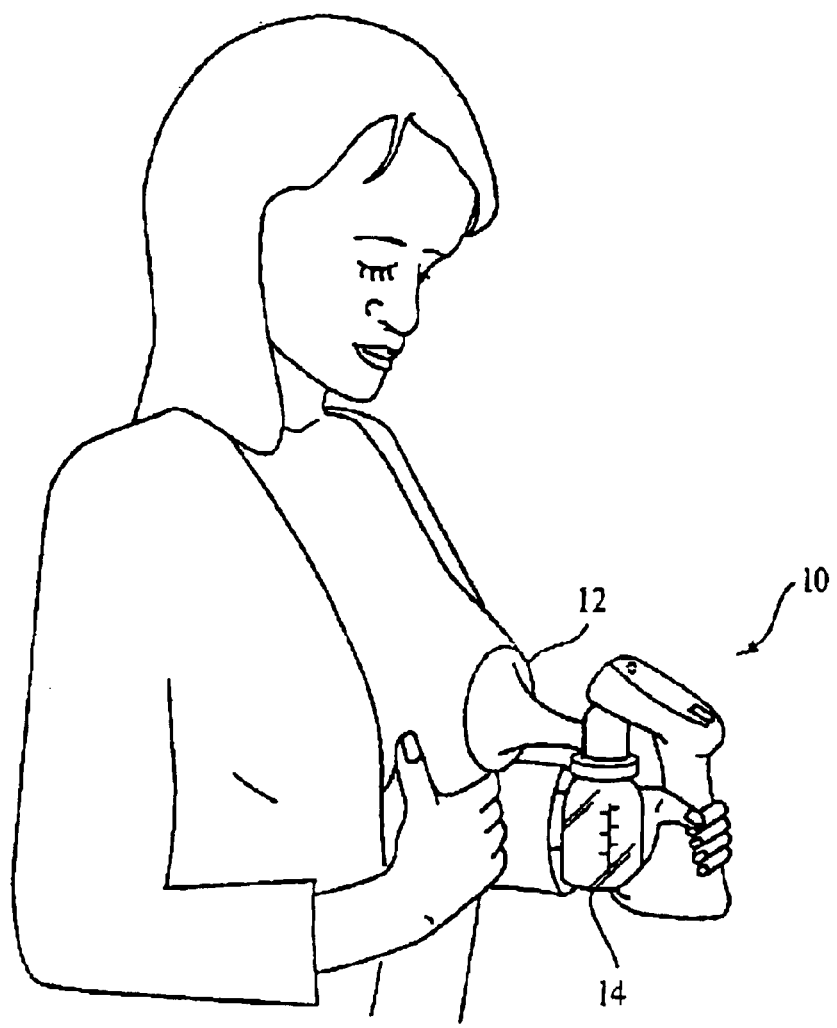
FIG. 1 illustrates the use of a portable breast pump.

Referring first to FIG. 1, electric breast pump 10 is operated by holding the hood 12 of the pump against the breast and turning the pump on. Once turned on, pump 10 automatically cycles vacuum pressure applied to the breast to simulate the natural sucking rhythms of an infant. Milk extracted from the breast flows from hood 12 into a removable storage bottle or receptacle 14. When turned off, the pump automatically releases hood vacuum for easy removal from the breast.

Figure 2:
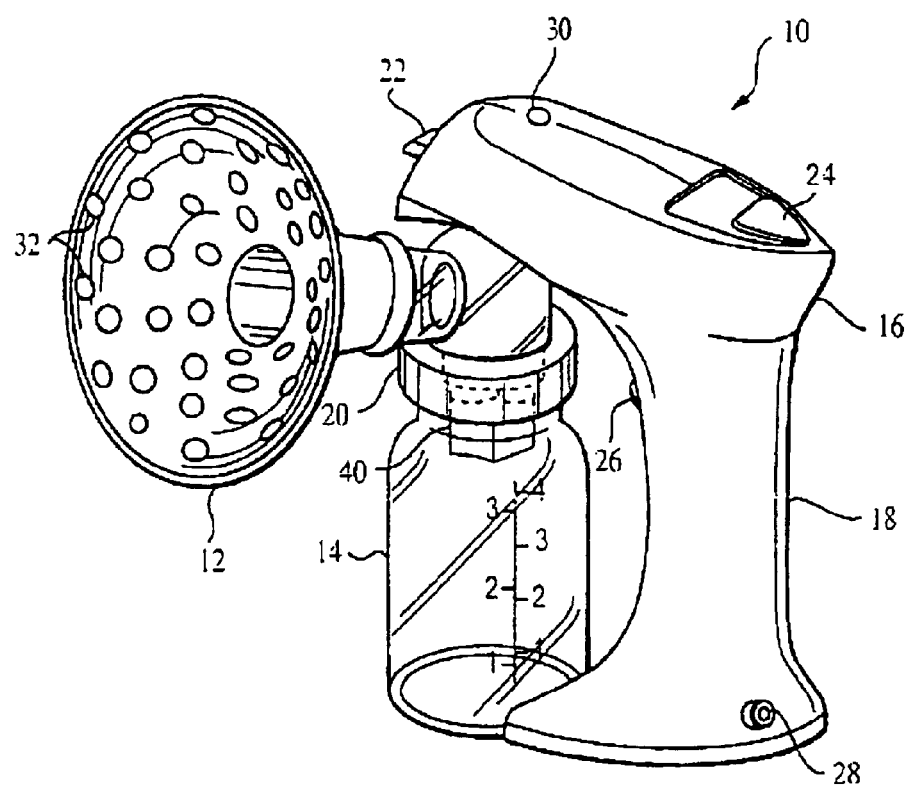
FIG. 2 is a perspective view of the breast pump.

Referring now to FIG. 2, the main body 16 of pump 10 forms a graspable handle 18 for holding the pump with one hand during operation. Bottle 14 is connected to body 16 and hood 12 by a 3-way adaptor or vacuum bulkhead 20, through which milk flows from hood 12 to bottle 14 through a valve cup 40. The bottle and hood are suspended from pump body 16 by bulkhead 20. which is released from body 16 by depressing a release plunger 22. The only two user operation controls provided on the pump are an on/off button 24 and a vacuum level adjustment dial 26, which is located on handle 18 for convenient manipulation during operation. Pump 10 is battery-operated, and a power jack 28 at the base of the pump is provided for connecting the pump to household current through a typical AC/DC converter (not shown).

A light-emitting diode (LED) 30 at the top of the pump helps to identify various operation modes. A blinking light during battery operation indicates that the batteries are running low on power. If battery use is continued past a predetermined low voltage level, the pump will automatically cease pumping and will release hood vacuum and turn off LED 30. A fast blinking LED 30 while the pump is plugged into an AC power outlet indicates that the batteries are being controllably drained to a very low voltage (or "refreshed") to improve recharge-ability. A slow blinking light while plugged in means that the batteries are being recharged. When fully recharged, LED 30 will be turned off.

Hood 12 is a flexible breast shield that is provided with inner bumps 32 that are designed to stimulate milk let down by creating a massaging effect during pumping pressure cycles.

Figure 3:
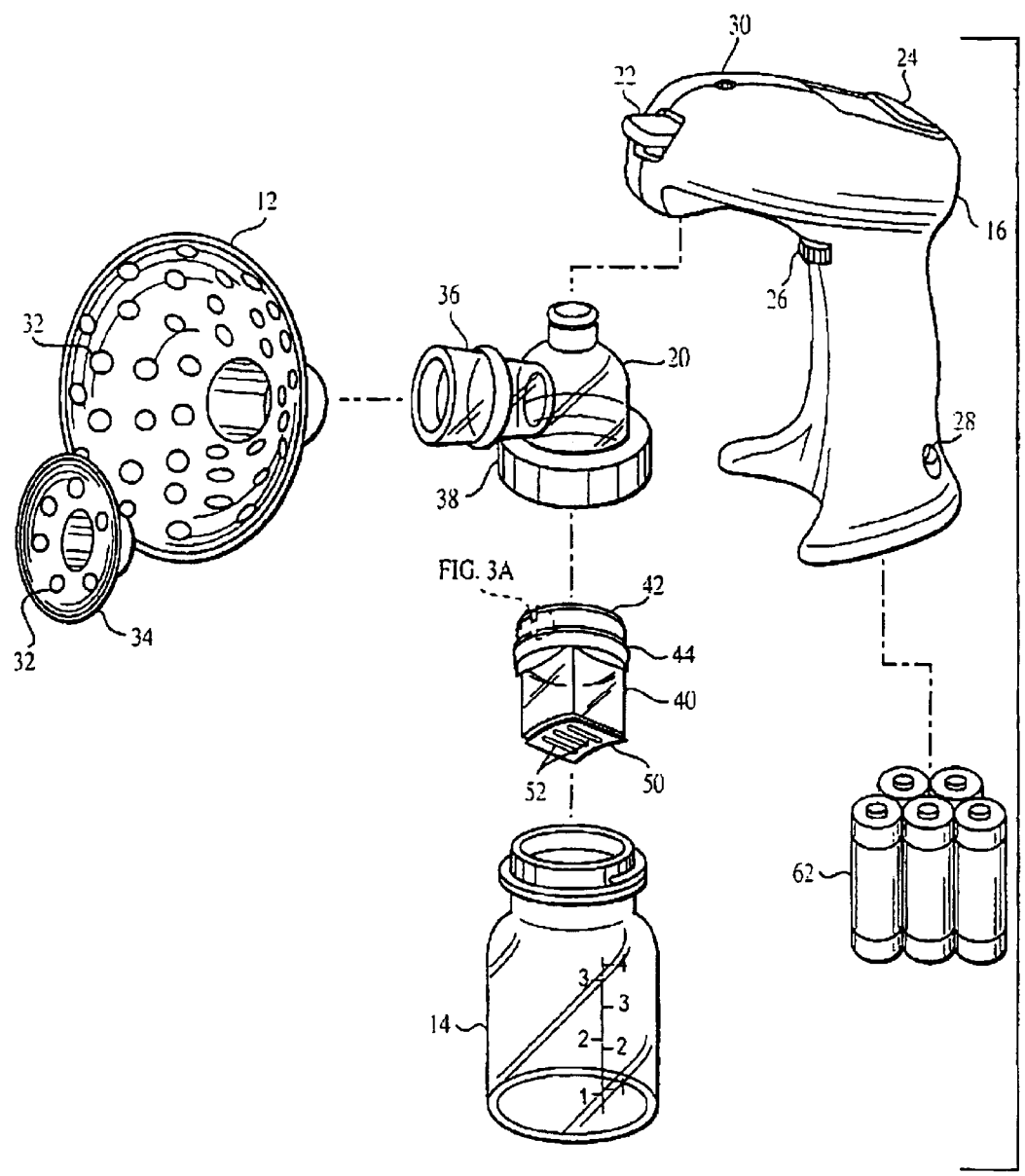
FIG. 3 is an expanded view of the major components of the pump.

Referring to FIG. 3, a nipple adaptor 34 is designed to be placed within hood 12 to accommodate smaller breasts or nipples, and is provided with additional massaging bumps 32. The nose of hood 12 is releasably pressed over an inlet conduit 36 of bulkhead 20 to form a vacuum-tight connection. Bulkhead 20 is molded of clear plastic and has a lower skirt 38 that makes a threaded connection with the top of bottle 14. A typical gasket (not shown) between bulkhead 20 and the upper edge of the top of bottle 14 makes the connection between bulkhead 20 and bottle 14 vacuumtight.

Figure 3A:
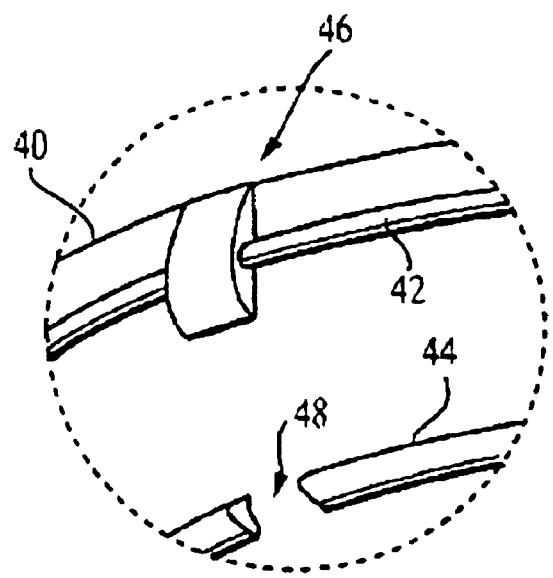
FIG. 3A is an enlarged view of area 3A in FIG. 3.

Before bulkhead 20 is threaded onto bottle 14, a valve cup 40 is releasably pressed into an inner bore of bulkhead 20 just above skirt 38. A small molded bead 42 about the periphery of the circular top of valve cup 40 provides a seal between the bulkhead 20 and cup 40 about most of the periphery of the cup. A larger bead 44 farther down on cup 40 limits the distance cup 40 is pressed into bulkhead 20 and helps to keep the cup from becoming cocked within the bulkhead. As shown in FIG. 3A. an arched, molded protrusion 46 extends axially across sealing bead 42 at one location about the cup perimeter, and projects radially outward from the side wall of the cup at its midpoint slightly farther than bead 42, creating two small air leak paths across the connection between bulkhead 20 (FIG. 3) and valve cup 40. A corresponding groove 48 through stop bead 44 ensures that bead 44 will not form a controlling seal between the bulkhead and valve cup. In effect, a fixed and small vacuum leak is created around the valve cup, the benefits of which are discussed below. Alternative air leak path constructions may be employed, such as a slit through bead 42 or a fixed orifice molded or pierced through the side of the valve cup body, for instance. Also, instead of providing air leak features on the valve cup, appropriate features may be provided on the inner surface of bulkhead 20 where the valve cup engages the bulkhead.

Referring back to FIG. 3, when assembled valve cup 40 extends from bulkhead 20 down into bottle 14 and forms a one-way valve between the bulkhead and the bottle. When vacuum is applied to the interior of bulkhead 20 and valve cup 40, a flexible flapper membrane 50 is drawn up to cover two slots 52 through the bottom of valve cup 40, thereby enabling the vacuum source of the pump to more quickly produce the desired level of vacuum at the breast by not evacuating the volume of bottle 14 below valve cup 40. During suction, milk flowing from hood 12 is collected in the valve cup. Upon release of vacuum pressure, the weight of collected milk in cup 40 helps to lower membrane 50 to let the collected milk drop into bottle 14. At the start of the next vacuum cycle, membrane 50 is again drawn against the lower surface of cup 40 to cover slotted holes 52 and enable rapid increase in hood vacuum.

Figure 4:
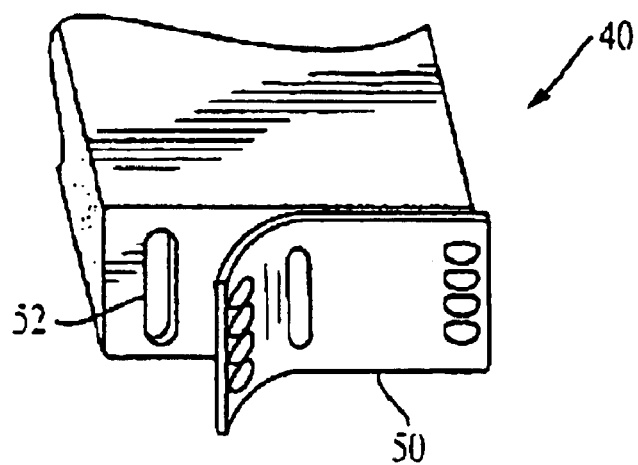
FIG. 4 is a perspective view of the lower end of the valve cup, showing the flapper membrane.

The lower end of valve cup 40 is illustrated in FIG. 4. The primary structure of cup 40 is molded of semi-rigid polypropylene with a bottom surface forming a gentle arc such that milk is directed toward a slot 52 formed through the lower surface of the cup near each of two opposite sides. Membrane 50 is formed of a resilient, flexible material and staked, snapped or otherwise fastened to the primary structure of the cup at its midpoint, such that it forms two freely cantilevered flaps corresponding to the two holes 52 in the bottom of the cup. In the illustrated embodiment, the membrane is of molded silicone rubber having a nominal thickness of about 0.025 inch (0.6 millimeter) and an extent of about ¾ inch by ¾ inch (20 millimeters per side). A molded projection from the upper surface of the membrane (not shown) is snapped into a corresponding hole in the bottom of the valve cup body. Raised bumps 54 opposite slots 52 help to add rigidity to the membrane flaps and help to avoid sucking the membrane too far into slots 52.

Referring back to FIGS. 3 and 3A, release of collected milk from valve cup 40 is aided by the fixed, small amount of leakage built into the seal between the valve cup and bulkhead 20 (described above with reference to the intersection of seal bead 42 and projection 46 of the valve cup). During the suction portion of the pumping cycle, during which the interior of bulkhead 20, valve cup 40 and hood 12 are evacuated, the fixed leakage about valve cup 40 enables a slow, progressive evacuation of air from the interior of bottle 14, creating by the end of the suction cycle a low level of vacuum within the bottle. When the vacuum in the bulkhead is rapidly released at the end of the suction cycle, the low level of vacuum in bottle 14, below valve cup 40, helps to pull membrane 50 away from slots 52 and to pull collected milk through the bottom of the valve cup and into bottle 14, such that valve cup 40 is quickly emptied before the next suction cycle. The amount of leakage designed into the seal between valve cup 40 and bulkhead 20 must be small enough to not inhibit a sufficiently rapid increase in vacuum (i.e., reduction in absolute pressure) in bulkhead 20 and at the breast at the beginning of the suction cycle, but large enough to form enough vacuum in the bottle to deflect membrane 50 away from the bottom of the valve cup and pull the collected milk from the valve cup during the release cycle. In this sense, the controlled leakage acts as a low-pass pressure filter between breast and bottle. The transparent bulkhead 20 and valve cup 40 enable the mother to watch the cyclic filling of the valve cup to monitor the rate and progress of milk extraction.

Figure 5:
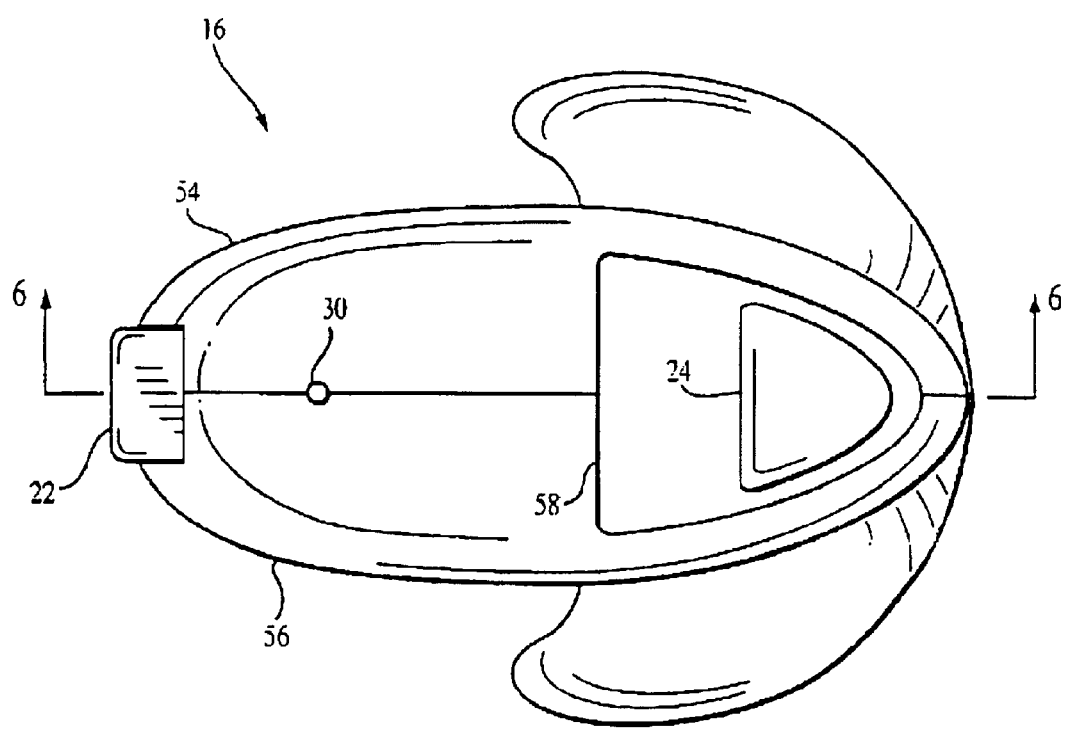
FIG. 5 is a top view of the main body of the breast pump.
Figure 6:
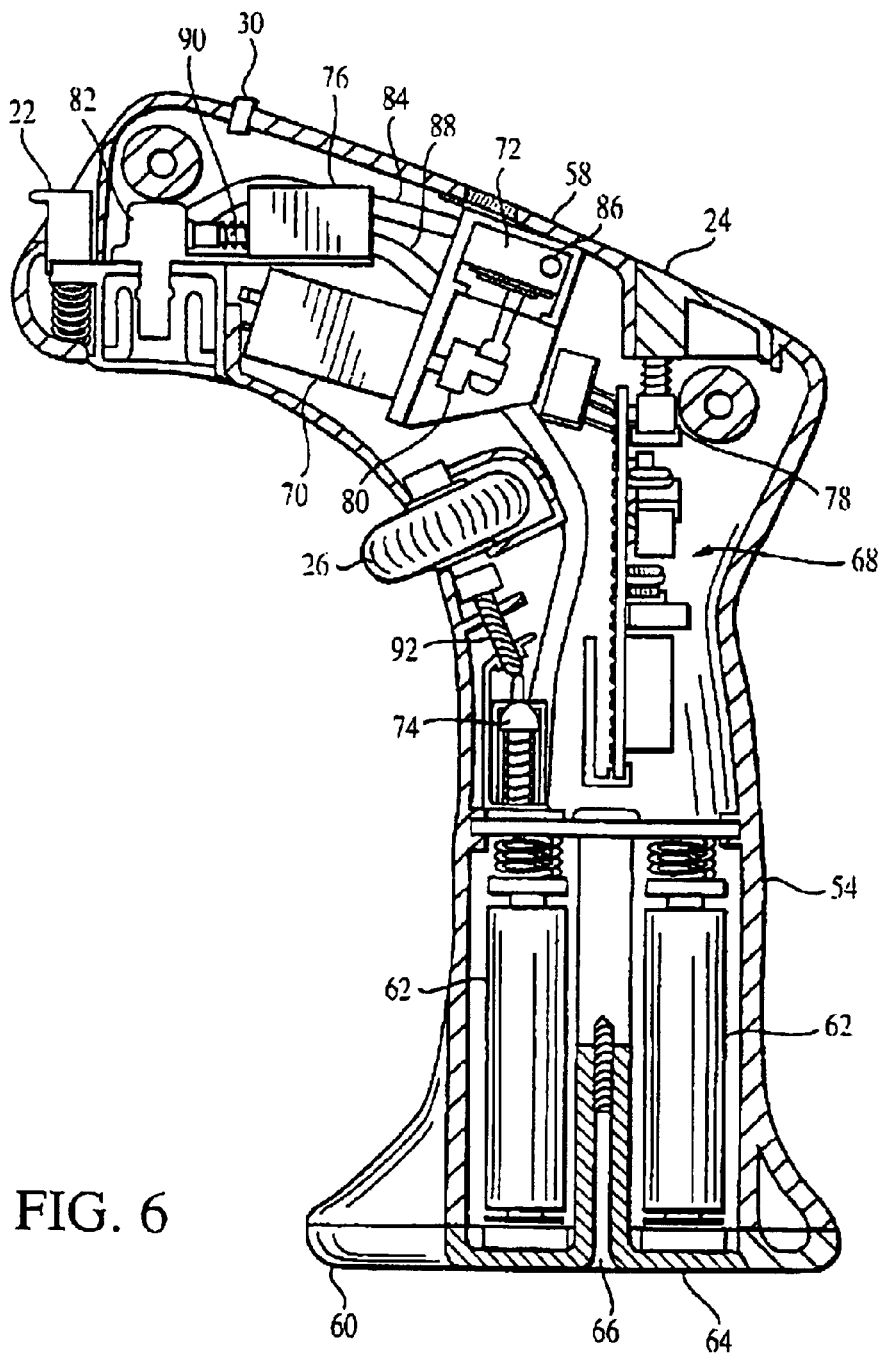
FIG. 6 is a cross-sectional view of the main body, taken along line 6—6 in FIG. 5.

Referring to FIGS. 5 and 6, the main body 16 of the breast pump 10 has a housing comprising left and right halves 54 and 56, an upper button plate 58 and a base plate 60. The handle of the unit accommodates five 1.5-volt rechargeable batteries 62 (shown also in FIG. 3), which are held in place by a removable battery cover 64 and threaded fastener 66. Other major internal components illustrated in FIG. 6 include the pump controller 68 in the form of a printed circuit board with discrete mounted components, an electric pump motor 70, a diaphragm pump 72, a needle valve 74 for adjusting pump vacuum level, and a solenoid 76 for releasing pump pressure.

When the unit is turned on, by pushing power button 24 to activate a power switch 78 mounted on the controller circuit board, motor 70 is energized to continuously run pump 72 until turned off, either by again pushing power button 24 or automatically by controller 68. An eccentric cam 80 translates rotary motion of the motor rotor into reciprocating motion of the push rod of diaphragm pump 72. Diaphragm pump 72 operates as a typical diaphragm pump, sucking air from valve manifold 82 through a flexible hose 84 during one half of each stroke cycle, and pushing air out of an outlet 86 during the other half of each stroke cycle. With the pump fully assembled, valve manifold 82 provides open parallel pneumatic communication between diaphragm pump 72. the bulkhead 20 (shown in FIG. 2, for instance), and needle valve 74. Connection to needle valve 74 is made by flexible tube 88. A release hole (not shown) in the side of manifold 82 is normally covered by the spring-loaded plunger 90 of solenoid 76, enabling diaphragm pump 72 to build vacuum pressure. When solenoid 76 is energized, plunger 90 retracts against its spring, exposing the manifold release hole to quickly release vacuum pressure at the breast. When solenoid 76 is again de-energized, its plunger reseals the release hole and the continuously running diaphragm pump again builds a suction pressure. Alternatively the solenoid may be configured to cover the release hole of the manifold when energized, and automatically retract to release vacuum when de-energized.

Needle valve 74 is adjusted by turning dial 26, thereby adjusting the extension of screw 92 and the corresponding depression of the plunger of the needle valve, thereby adjusting the controlled vacuum leakage through the needle valve from manifold 82. Alternatively an adjustable pressure relief valve may be employed, which would permit vacuum leakage only when an adjustable vacuum level is exceeded.

Bulkhead release button 22 operates a bulkhead attachment/release mechanism similar to that of the "1068 Breast Pump" marketed by The First Years Inc. in Avon, Mass. The attachment/release mechanism allows the bulkhead to be quickly and sealingly attached to the pumping system by simply pushing the bulkhead upward until it snaps into place. Releasing the attached bulkhead requires depressing release button 22.

Controller 68 contains a timer circuit for controlling the frequency and interval durations of the repeating vacuum pressure cycles based on time. In the illustrated embodiment, the timer circuit hardware is included in an EPROM integrated circuit chip NT66P20 that is programmed to provide the desired control functions. Other devices and methods of monitoring time, such as with various sorts of oscillators, are also known to those of skill in the art of circuit design. Preferably, the method of monitoring (i.e., measuring or tracking) time is essentially independent of pump pressures, flow rates, motor or pump temperatures, and expected variations in physical component characteristics and conditions, such that the desired sucking rhythm is accurately maintained, even as battery voltages begin to drop.

Controller 68 has four primary functions. First, it provides constant power to motor 70 while the unit is turned on. Second, it controls the timing of solenoid 76 to establish and maintain the alternating suction/release rhythm. Third, it operates indicator 30 to communicate information about the operational status of the unit. Fourth, it monitors battery voltage and initiates controlled discharge and recharge as appropriate. Fifth, it initiates a controlled automatic shutdown when necessary.

The first three controller functions have already been discussed. When the unit is turned off but plugged into an AC outlet, controller 68 monitors battery voltage to determine whether or not to recharge, or controllably discharge and then recharge, the batteries. In addition, the controller 68 monitors battery voltage every 3 seconds during motor operation. When battery voltage is below a first threshold but above a lower, second threshold, the controller causes the illuminated LED 30 to blink. To avoid premature LED blinking from transient low voltage conditions, controller 68 must identify a low voltage condition at least 30 times before causing LED 30 to blink. When voltage drops below the second threshold for at least 4 to 6 consecutive voltage measurements, controller 68 determines that battery voltage has fallen too low to permit safe, continued operation of the unit within desirable performance specifications and initiates an automatic shutdown. Before shutting down completely, controller 68 first energizes solenoid 76 for 2 seconds to release any residual vacuum at the breast to facilitate removal of the breast hood.

Figure 7:
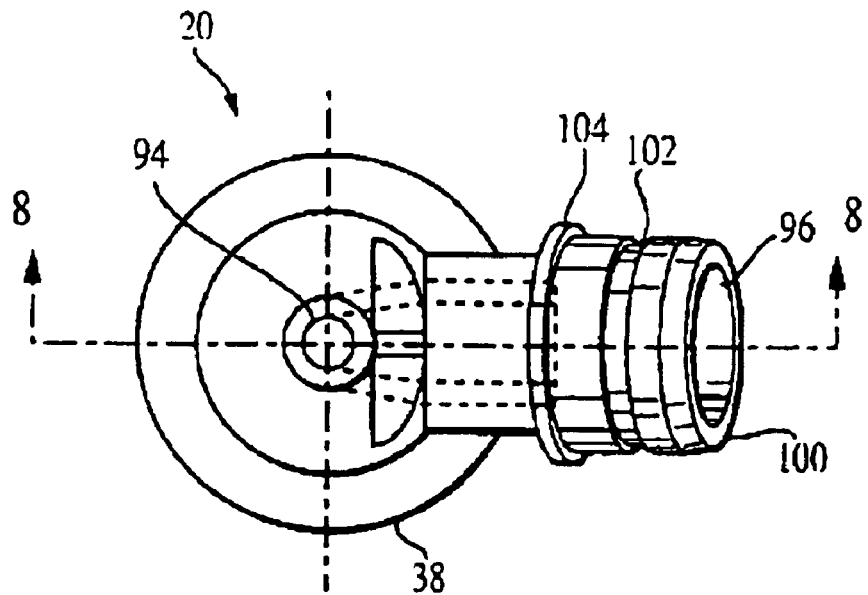
FIG. 7 is a top view of the bulkhead of the breast pump.
Figure 8:
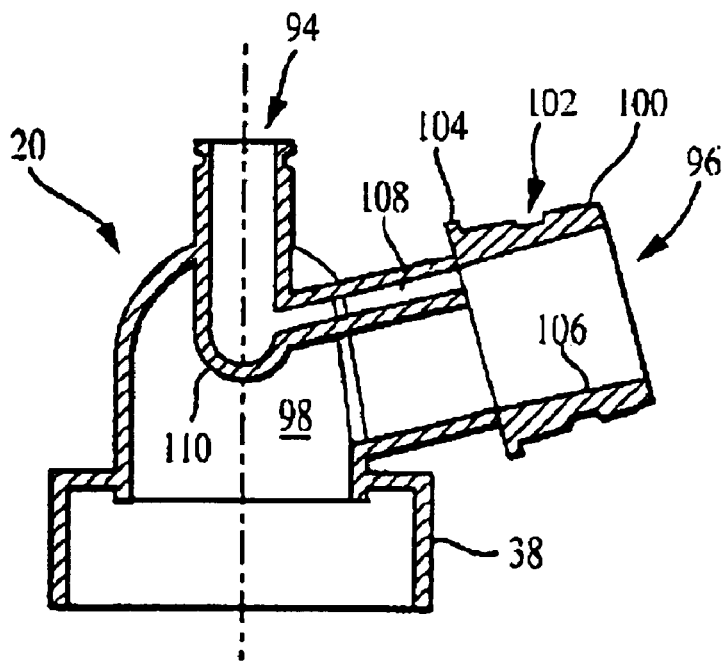
FIG. 8 is a cross-sectional view of the bulkhead, taken along line 8—8 in FIG. 7.

Referring to FIGS. 7 and 8, bulkhead 20 is unitarily molded of clear polycarbonate and provides a sealed hydraulic connection between the pump vacuum source (through an upper vacuum port 94), the breast hood (through a milk inlet 96) and the bottle (threadably connected to lower bulkhead skirt 38). Bulkhead 20 defines an internal chamber 98 that is evacuated during, the suction portion of the pressure cycle. The milk inlet conduit 100 has a molded groove 102 for receiving an internal rib of the breast hood (not shown) and a stop shoulder 104. The milk inlet extends from one side of internal chamber 98 when the bulkhead is mounted on the pump in an upright position for normal use (skirt down), such that entering milk tends to flow along lower side 106 of inlet conduit 100. Notably, communication between chamber 98 and vacuum port 94 is through a vacuum inlet passage 108 that extends a distance toward and along milk inlet conduit 100. Vacuum inlet passage 108 is well above the lower side of the conduit, such that with the pumping device in its upright position milk entering from the hood will tend to avoid the vacuum inlet passage. With the pump in a sideways position with milk inlet conduit 100 extending upward, such as if the unit falls onto its side opposite the breast hood, the open end of inlet passage 108 is high enough to prevent milk from the bottle from flowing into the vacuum inlet passage 108 and contaminating or wetting components of the pump vacuum source. Additionally, inner baffle 110 helps to protect the vacuum source from milk spray or splash, such as if the unit is inadvertently shaken or dropped. Bulkhead 20 may be employed to advantage with many types of electric or manual breast pumps, and is particularly useful with portable units that are prone to being dropped, tilted or shaken.

Other embodiments are within the scope of the invention, as defined by the appended claims. For example, rhythm adjustment means may be added, such as in the form of dials or screws, for adjusting the timing of the suction and release portions of the cycle as controlled by the controller.

What is claimed is:

1. A pumping device for drawing milk from a human breast, the pumping device comprising
    a milk receptacle in fluid communication with a hood adapted to receive a human breast;
    an electric motor configured to drive a pump to produce sub-atmospheric pressure in the hood to pull milk from the breast;
    an electrically operated valve between the pump and the hood and adapted to, in a suction position, expose the breast to sub-atmospheric pressure generated by the pump to apply suction to the breast and to, in a release position, at least partially block the breast from sub-atmospheric pressure generated by the pump to reduce the suction applied to the breast;
    a controller adapted to track time and to, as a function of tracked time, move the valve between its suction and release positions at predetermined time intervals, so as to produce repeating pressure cycles in the cup to simulate infant nursing; and
    a manual suction adjuster to enable a user to manually adjust the sub-atmospheric pressure applied to the breast with the valve in its suction position.

2. The pumping device of claim 1 further comprising an electrical storage battery for supplying electrical power to activate the motor and valve and wherein the produced pressure cycles are of consistent timing over a useful range of battery voltage and motor speed.

3. The pumping device of claim 2 wherein the controller is adapted to monitor battery voltage and to automatically cease powering the motor at a predetermined low battery voltage.

4. The pumping device of claim 3 comprising an indicator to alert a user that battery voltage is above said low battery voltage but below a predetermined warning voltage.

5. The pumping device of claim 2 wherein the controller is adapted to monitor voltage of the battery and to automatically move the valve to its release position in response to the battery voltage falling below a predetermined low voltage threshold.

6. The pumping device of claim 2 further comprising a jack to receive electrical power from an external power source.

7. The pumping device of claim 6 wherein the controller includes a battery recharging circuit for recharging the battery with electrical power from the external power source.

8. The pumping device of claim 7 wherein the controller is adapted to substantially discharge the batteries before recharging for improved recharge capacity.

9. The pumping device of claim 1 adapted to be powered from an external alternating current power source.

10. The pumping device of claim 1 wherein the repeating pressure cycles each comprises a suction phase of between about 2 and 2.5 seconds, followed by a release phase of about 1 second.

11. The pumping device of claim 1 wherein the suction adjuster comprises a bleeder valve operable by turning a suction control dial.

12. The pumping device of claim 1 comprising a bulkhead connecting the milk receptacle to the pump and hood, the bulkhead having a housing defining
    an internal chamber;
    a milk inlet conduit providing communication between the hood and the internal chamber, the milk inlet conduit extending from one side of the internal chamber with the pumping device in an upright position for normal use, such that entering milk tends to flow along a lower side of the conduit;
    a milk outlet providing communication between the internal chamber and the milk receptacle, the milk outlet disposed at a lower end of the internal chamber with the portable pumping device in said upright position; and
    a vacuum port providing communication between the pump and the internal chamber through a vacuum inlet passage within the receptacle bulkhead, the vacuum inlet passage extending a distance toward the milk inlet conduit and separated from the lower side of the conduit, such that with the pumping device in its upright position milk entering from the hood will tend to avoid the vacuum inlet passage and, with the pumping device in a sideways position with the milk inlet conduit extending upward, milk from the receptacle will be inhibited from entering the vacuum inlet passage.

13. The pumping device of claim 12 wherein the internal chamber has a domed upper surface and the vacuum port is disposed at an upper apex of the domed upper surface.

14. The pumping device of claim 12 wherein the housing is a unitary molded piece of plastic.

15. The pumping device of claim 12 forming a top for the milk receptacle, the milk outlet comprising a threaded connection between the milk receptacle and the bulkhead housing.

16. The pumping device of claim 12 wherein the vacuum inlet passage extends beyond the milk outlet toward the hood.

17. The pumping device of claim 1 further comprising a one-way valve disposed between the hood and the milk receptacle, the valve comprising
    a cup-shaped valve body with a hole through a bottom thereof; and
    a flexible membrane flap arranged to
        cover the hole through the valve body when suction is applied to the hood, inhibiting flow between the hood and the milk receptacle, such that milk from the hood is collected in the cup on top of the membrane flap, and to
        flex, under weight of the collected milk, to expose the hole when hood suction is released, allowing the collected milk to flow from the valve body into the milk receptacle.

18. The pumping device of claim 17, wherein the valve cup is retained in a bulkhead constructed to provide communication between the hood, the milk receptacle, and the vacuum source, with the valve cup engaging the bulkhead at an interface constructed to provide a predetermined amount of air leakage around the valve, between the bulkhead and the milk receptacle, when suction is applied to the hood.

19. A method of extracting milk from a human breast, the method comprising
    holding the hood of the pumping device of claim 1 against the breast; and
    activating the pumping device to begin applying repeating pressure cycles to the breast to extract milk, the controller of the pumping device regulating frequency of the pressure cycles to be effectively independent of suction, flow rates and power levels.

20. A pumping device for drawing milk from a human breast, the pumping device comprising
    a milk receptacle in fluid communication with a hood adapted to receive a human breast;
    an electric motor configured to drive a pump to produce sub-atmospheric pressure in the hood to pull milk from the breast;
    an electrically operated valve between the pump and the hood and adapted to, in a suction position, expose the breast to sub-atmospheric pressure generated by the pump to apply suction to the breast and to, in a release position, at least partially block the breast from sub-atmospheric pressure generated by the pump to reduce the suction applied to the breast; and
    a controller adapted to track time and to, as a function of tracked time, move the valve between its suction and release positions at predetermined time intervals, so as to produce repeating pressure cycles in the cup to simulate infant nursing; and
    a bulkhead connecting the milk receptacle to the pump and hood, the bulkhead having a housing defining
    an internal chamber;
    a milk inlet conduit providing communication between the hood and the internal chamber, the milk inlet conduit extending from one side of the internal chamber with the pumping device in an upright position for normal use, such that entering milk tends to flow along a lower side of the conduit;
    a milk outlet providing communication between the internal chamber and the milk receptacle, the milk outlet disposed at a lower end of the internal chamber with the portable pumping device in said upright position; and
    a vacuum port providing communication between the pump and the internal chamber through a vacuum inlet passage within the receptacle bulkhead, the vacuum inlet passage extending a distance toward the milk inlet conduit and separated from the lower side of the conduit, such that with the pumping device in its upright position milk entering from the hood will tend to avoid the vacuum inlet passage and, with the pumping device in a sideways position with the milk inlet conduit extending upward, milk from the receptacle will be inhibited from entering the vacuum inlet passage.

21. The pumping device of claim 20 wherein the internal chamber has a domed upper surface and the vacuum port is disposed at an upper apex of the domed upper surface.

22. The pumping device of claim 20 wherein the housing is a unitary molded piece of plastic.

23. The pumping device of claim 20 forming a top for the milk receptacle, the milk outlet comprising a threaded connection between the milk receptacle and the bulkhead housing.

24. The pumping device of claim 20 wherein the vacuum inlet passage extends beyond the milk outlet toward the hood.

25. A pumping device for drawing milk from a human breast, the pumping device comprising
    a milk receptacle in fluid communication with a hood adapted to receive a human breast;
    an electric motor configured to drive a pump to produce sub-atmospheric pressure in the hood to pull milk from the breast;
    an electrically operated valve between the pump and the hood and adapted to, in a suction position, expose the breast to sub-atmospheric pressure generated by the pump to apply suction to the breast and to, in a release position, at least partially block the breast from sub-atmospheric pressure generated by the pump to reduce the suction applied to the breast;
    a controller adapted to track time and to, as a function of tracked time, move the valve between its suction and release positions at predetermined time intervals, so as to produce repeating pressure cycles in the cup to simulate infant nursing; and
    a one-way valve disposed between the hood and the milk receptacle, the valve comprising a cup-shaped valve body with a hole through a bottom thereof, and a flexible membrane flap arranged to cover the hole through the valve body when suction is applied to the hood, inhibiting flow between the hood and the milk receptacle, such that milk from the hood is collected in the cup on top of the membrane flap, and to flex, under weight of the collected milk, to expose the hole when hood suction is released, allowing the collected milk to flow from the valve body into the milk receptacle.

26. The pumping device of claim 25, wherein the valve cup is retained in a bulkhead constructed to provide communication between the hood, the milk receptacle, and the vacuum source, with the valve cup engaging the bulkhead at an interface constructed to provide a predetermined amount of air leakage around the valve, between the bulkhead and the milk receptacle, when suction is applied to the hood.

27. The pumping device of claim 25 wherein the repeating pressure cycles each comprises a suction phase of between about 2 and 2.5 seconds, followed by a release phase of about 1 second.

* * * * *